United States Patent [19]

Henkin

[11] 4,334,533
[45] Jun. 15, 1982

[54] BREATHING METHOD AND APPARATUS FOR SIMULATING HIGH ALTITUDE CONDITIONS

[76] Inventor: Melvyn L. Henkin, 5011 Donna Ave., Tarzana, Calif. 91356

[21] Appl. No.: 155,193

[22] Filed: Jun. 2, 1980

Related U.S. Application Data

[63] Continuation-in-part of Ser. No. 901,621, May 1, 1978, Pat. No. 4,210,137, which is a continuation-in-part of Ser. No. 646,424, Jan. 5, 1976, Pat. No. 4,086,923.

[51] Int. Cl.³ .............................................. A62B 7/10
[52] U.S. Cl. ............................. 128/205.28; 128/914; 128/206.15
[58] Field of Search .................. 128/200.24, 203.12, 128/202.26, 203.25, 203.28, 203.29, 205.17, 205.12, 205.11, 205.22, 205.25, 205.28, 914, 206.15

[56] References Cited

U.S. PATENT DOCUMENTS

| 244,062 | 7/1881 | Khotinsky | 128/205.17 |
| 1,589,463 | 6/1926 | Drager | 128/205.22 |
| 3,195,538 | 7/1965 | Galeazzi | 128/205.12 |
| 3,556,097 | 1/1971 | Wallace | 128/203.28 |
| 3,575,167 | 4/1971 | Michielsen | 128/205.28 |
| 4,155,361 | 5/1979 | Mascher | 128/202.26 |
| 4,210,137 | 7/1980 | Henkin | 128/200.24 |

FOREIGN PATENT DOCUMENTS

447119  5/1936  United Kingdom ........... 128/205.28

Primary Examiner—Henry J. Recla
Attorney, Agent, or Firm—Freilich, Hornbaker, Wasserman, Rosen & Fernandez

[57] ABSTRACT

An improved breathing method and apparatus for enabling a user, while at a first altitude, e.g. sea level, to experience higher altitude conditions. The apparatus includes an inspiratory tube and an expiratory tube and means for mixing a portion of oxygen-reduced expired air with ambient air to supply air for inspiration. The first ends of the inspiratory and expiratory tubes are coupled to the users airway through a user breathing means. The remote end of the expiratory tube is coupled through a (carbon dioxide) $CO_2$ absorber canister to an air storage reservoir. The remote end of the inspiratory tube is also coupled through a $CO_2$ absorber canister to the reservoir for pulling oxygen-reduced air therefrom. The user breathing means includes a selectively dimensioned orifice to the environment so that on expiration, a predetermined portion of the user's expired air is exhausted to the environment while the remainder passes through $CO_2$ absorber material into the reservoir. On inspiration, air stored in the reservoir is pulled through $CO_2$ absorber material and combined with ambient air pulled into the breathing means through the orifice. Different size orifices can be utilized to simulate different altitudes.

18 Claims, 14 Drawing Figures

BREATHING METHOD AND APPARATUS FOR SIMULATING HIGH ALTITUDE CONDITIONS

RELATED APPLICATIONS

This application is a continuation-in-part of U.S. Application Ser. No. 901,621, filed May 1, 1978, now U.S. Pat. No. 4,210,137, which is a continuation-in-part of U.S. Application Ser. No. 646,424, filed Jan. 5, 1976, now U.S. Pat. No. 4,086,923.

BACKGROUND OF THE INVENTION

This invention relates generally to a breathing method and apparatus for supplying air to a user at one altitude so as to simulate conditions at a higher altitude.

Persons who ordinarily function at a near-sea-level altitude frequently experience headache, shortness of breath, nausea, sleeplessness, and reduced endurance during the initial days at higher altitude, e.g. above 7,500 feet. These factors are, in large part, attributable to the diminishing amount of oxygen available as altitude increases. A typical situation involves a sea-level resident who occassionally takes a skiing weekend above 7,500 feet. As altitude increases, oxygen availability diminishes, thus requiring the person to breathe deeper in an effort to supply sufficient oxygen to his bloodstream. The partial pressure of oxygen ($PO_2$) at 7,500 feet is only 75% (of the $PO_2$ at sea level) and at 10,000 feet is only 65%. At 19,000 feet, the $PO_2$ is only 50%, thus meaning that a unit volume of air at 19,000 feet contains only half as much oxygen as that same unit volume at sea level. Typically, after a few days at the higher altitude, the person will become acclimated and the aforementioned problems subside. Interestingly, evidence suggests that persons who experience high altitudes on a frequent and regular basis appear to maintain a certain degree of acclimation to the altitude and are considerably better able to avoid the aforementioned problems than infrequent visitors.

Applicant's parent and grandparent applications disclose a breathing method and apparatus for enabling a user, while at low altitudes, e.g. sea level, to experience higher altitude conditions.

Briefly, the apparatus disclosed in Applicant's prior applications, include inspiratory and expiratory tubes having first ends coupled to a breathing means which may include a mouth and/or nose mask. The remote end of the expiratory tube is coupled through a proportioning means to the environment and to a reservoir or air storage chamber. The remote end of the inspiratory tube is also coupled to the proportioning means so as to pull ambient air from the environment, as well as oxygen reduced air from the reservoir. By varying the proportioning means, the ratio of ambient air to expired air, and thus the oxygen concentration of the inspired air, is varied so as to enable the user to select a particular elevated altitude to be simulated. Carbon dioxide ($CO_2$) absorber material is incorporated in the system to remove $CO_2$ from the air drawn from the reservoir for inspiration by the user.

SUMMARY OF THE INVENTION

The present invention is directed to an improved method and apparatus for supplying air to a user at one altitude so as to simulate conditions at a higher altitude. These improvements are primarily directed toward achieving (1) a more compact and portable apparatus, (2) a lower resistance air flow path, and (3) greater assurance that the apparatus will be properly and safely used.

Apparatus in accordance with the present invention includes an inspiratory tube and an expiratory tube whose first ends are coupled to a user's airway through a breathing means, which may include a mask or mouthpiece. The remote end of the expiratory tube is coupled to a reservoir for storing oxygen-reduced expired air. The remote end of the inspiratory tube is also coupled to the reservoir for drawing air therefrom.

An exemplary embodiment of the invention is configured so as to be sufficiently compact to enable it to be comfortably worn by a user while walking, jogging, or performing other exercises. The compact configuration is in part attributable to the provision of a orifice to the environment located in the flowpath proximate to the user for exhausting a portion of the user expired air and for drawing ambient air from the environment for inspiration. The orifice is preferably formed in the user breathing means; e.g. in the mask, mouthpiece or connector, coupled to the inspiratory and expiratory tubes. In accordance with an exemplary embodiment, the breathing means is adapted to receive different removable inserts, each of which defines a different precisely dimensioned fixed orifice.

In accordance with the invention, $CO_2$ absorber material is incorporated in the inspiratory and/or expiratory flowpaths which are configured so as to exhibit low flow resistance. In an exemplary embodiment, the inspiratory and expiratory flowpaths are balanced and include like amounts of $CO_2$ absorbing material; i.e. approximately the same amount of $CO_2$ absorbing material is incorporated between the expiratory tube and reservoir as in incorporated between the reservoir and inspiratory tube.

In accordance with a further feature of an exemplary embodiment, the breathing means for communicating with a users airway includes a port defining the orifice to the environment and first and second ported arms for coupling to the first ends of the inspiratory and expiratory tubes, respectively. The arms are preferably mounted so that they can swivel to allow the breathing apparatus to be conveniently worn by the user adjacent either the users front or back.

In accordance with a still further feature of an exemplary embodiment, a backpad assembly is provided particularly configured to mount the breathing apparatus thereon to enable a user to readily carry the apparatus while exercising.

BRIEF DESCRIPTION OF THE FIGURES

FIG. 4 is a plan view, partially broken away, showing the flowpaths through an apparatus in accordance with the present invention;

DESCRIPTION

Figures 1, 2, 3:
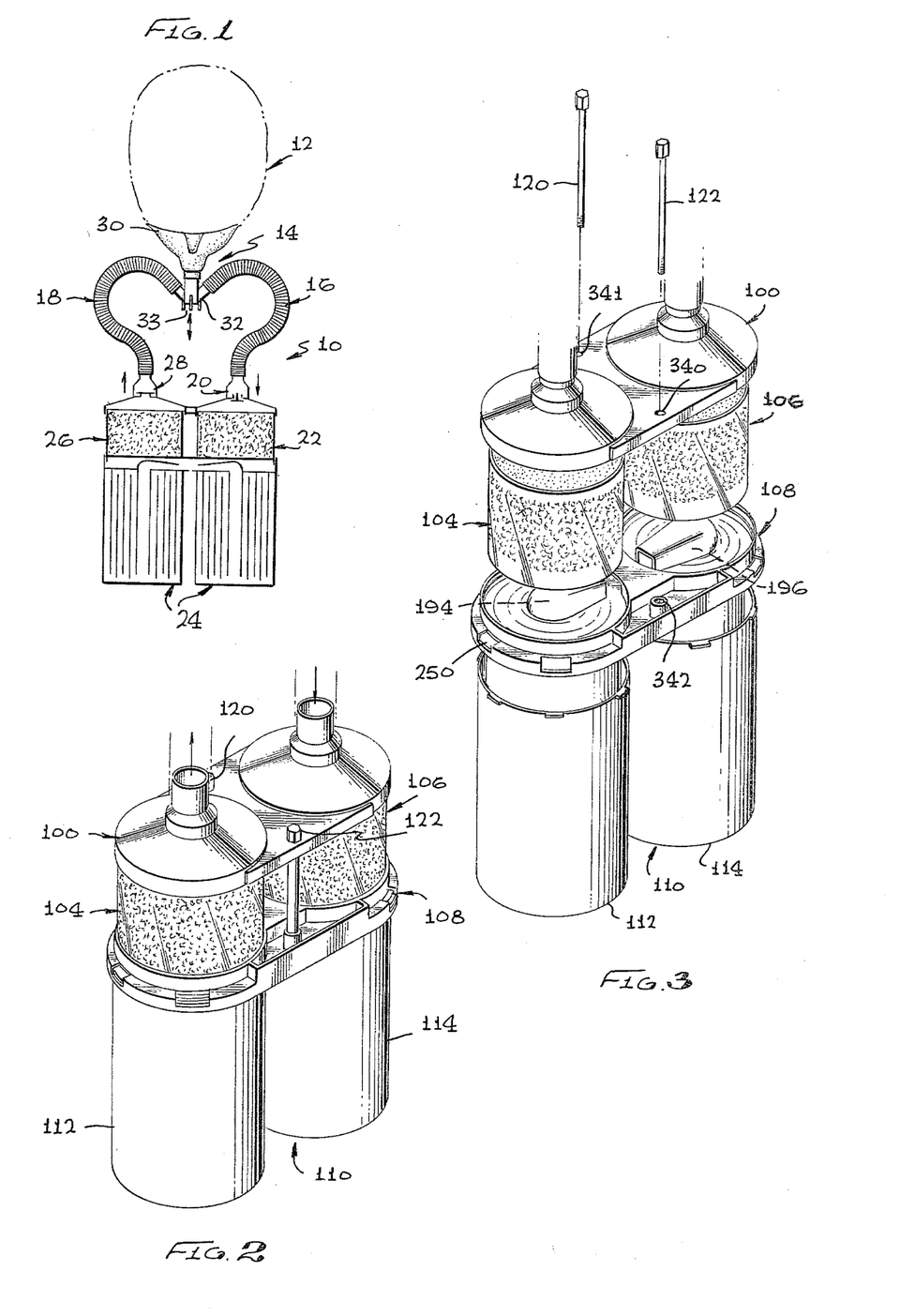
FIG. 1 is a schematic diagram of an exemplary embodiment of the invention in use.
FIG. 2 is a perspective view of an exemplary embodiment of the invention.
FIG. 3 is an exploded view of the apparatus illustrated in FIG. 2.
Figure 2:
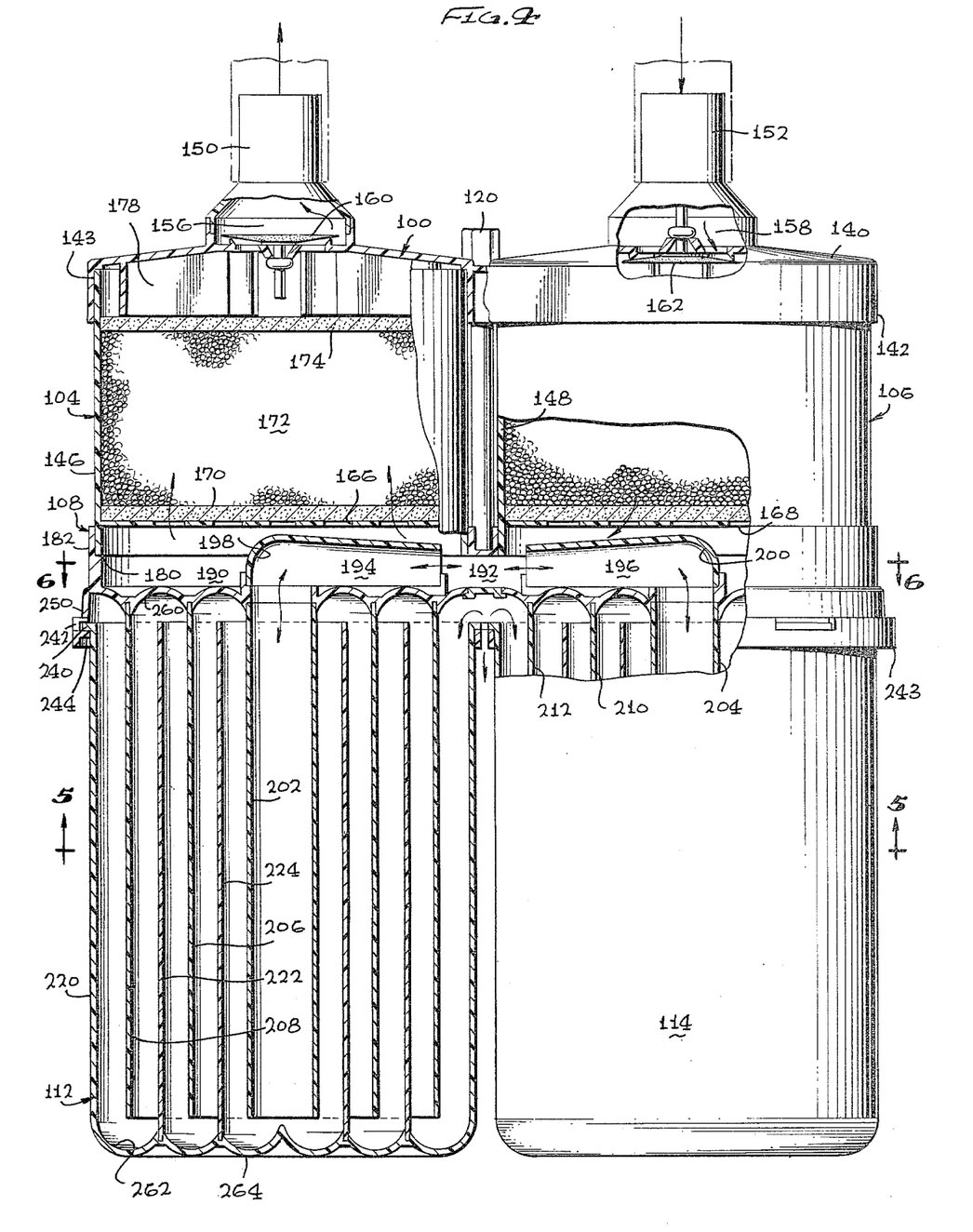
Figure 5:
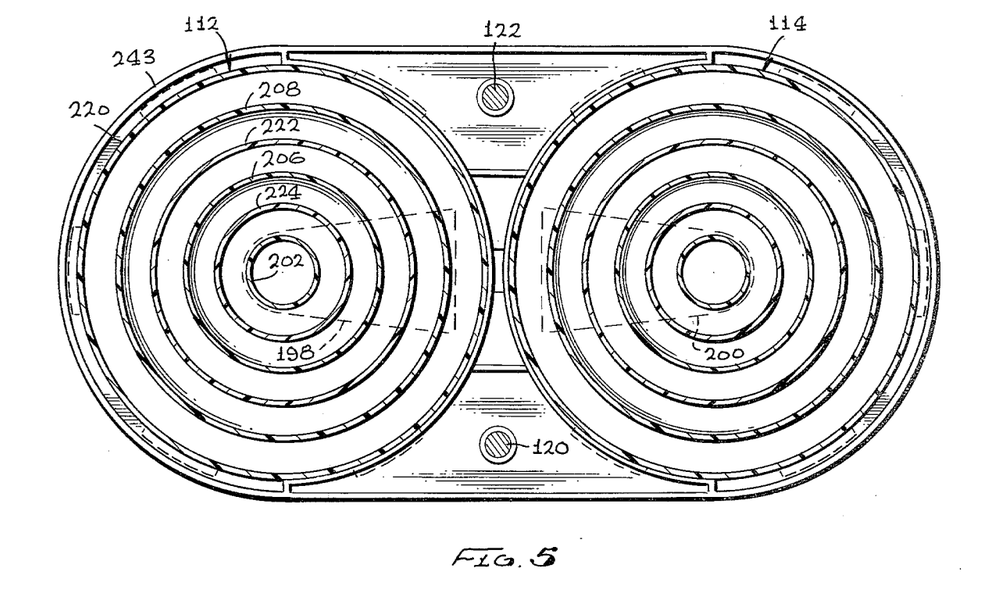
FIG. 5 is a sectional view taken substantially along the plane 5—5 of FIG. 4.
Figure 6:
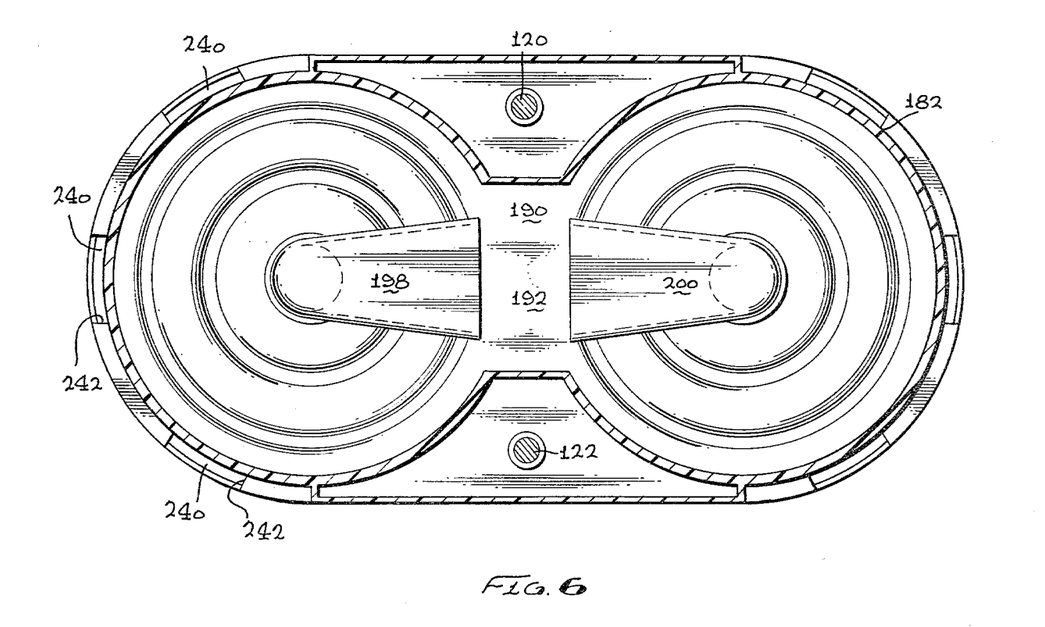
FIG. 6 is a sectional view taken substantially along the plane 6—6 of FIG. 4.

Attention is now directed to FIG. 1 which schemetically illustrates a breathing apparatus 10 in accordance with the present invention useful for simulating higher altitude breathing conditions for a user 12. Briefly, the apparatus 10 is comprised of a user breathing means 14 which communicates the users airway with an expiratory path and an inspiratory path. As will be discussed in detail hereinafter, on expiration, a portion of the users expired air is exhausted to the environment and the remainder of the expired air is stored in a reservoir. On inspiration, the stored air is drawn from the reservoir and mixed with ambient air and supplied to the user. Carbon dioxide ($CO_2$) absorber material is incorporated in the inspiratory and/or expiratory flowpaths to reduce the $CO_2$ content of the expired air prior to rebreathing.

In the schematically illustrated embodiment of FIG. 1, the expiratory path is defined by tube 16 which communicates through an expiratory valve 20 with a first quantity of $CO_2$ absorber material 22. Air passing through the $CO_2$ absorber material 22 is delivered into an air storage reservoir 24. The reservoir 24 also communicates with a second quantity of $CO_2$ absorber material 26. Air drawn through the absorber material 26 moves past an inspiratory valve 28 into the inspiratory tube 18.

The user breathing means 14 illustrated in FIG. 1 includes a breathing mask 30 and a connector 32. The connector 32 is provided with four ports; the first and second ports respectively communicate with the expiratory and inspiratory tubes 16, 18, the third port 33 communicates with the environment for passing ambient air therethrough and the fourth port communicates with the users airway.

In the use of the apparatus 10 of FIG. 1, on expiration, a portion of the users expired air will be exhausted directly to the environment through the third port 33 in the connector 32. The remaining portion of the users expired air will flow through the expiratory tube 16, and thence through the $CO_2$ absorber material 22 into the reservoir 24. On inspiration, the air stored in the reservoir is drawn through the $CO_2$ absorber material 26 to further reduce its $CO_2$ content and thence through the inspiratory tube 18 where it is combined with ambient air drawn into the connector 32 from the third port 33. Since the air inspired from the tube 18 has a considerably lower oxygen concentration than the ambient air, the air inspired by the user from the connector, will have a significantly lower concentration than the ambient air and thus will simulate air at a higher altitude than the environment. The inspired air however will not have a significantly higher $CO_2$ concentration than air naturally found at the simulated environment since the $CO_2$ in the users expired air is substantially removed by the $CO_2$ absorber material 22 and 26. The particular altitude which can be simulated by the method and apparatus depicted in FIG. 1 is dependent primarily upon the dimensions of the various ports in connector 32 which determines the ratio of ambient air to rebreathed air inspired by the user 12.

Attention is now directed to FIGS. 2–8 which illustrate the details of an exemplary embodiment of breathing apparatus in accordance with the present invention. The apparatus of FIGS. 2–7 is comprised primarily of a cover part 100, a pair of $CO_2$ absorber material canisters 104 and 106, a center part 108, and a pair of cup-like bottom members 112 and 114. As is depicted in FIGS. 2–4, the cover part 100 fits over and covers the canisters 104 and 106. The canisters 104 and 106 are seated within compartments defined in the center part 108. Bolts 120 and 122 fasten the cover part 100 and center part 108 together so as to tightly sandwich the canisters 104 and 106 therebetween. The cup-like members 112 and 114 are then secured to the underportion of the center part 108 to define an air storage reservoir having a series of flow path segments therein, as will be explained in greater detail hereinafter.

Figure 7:
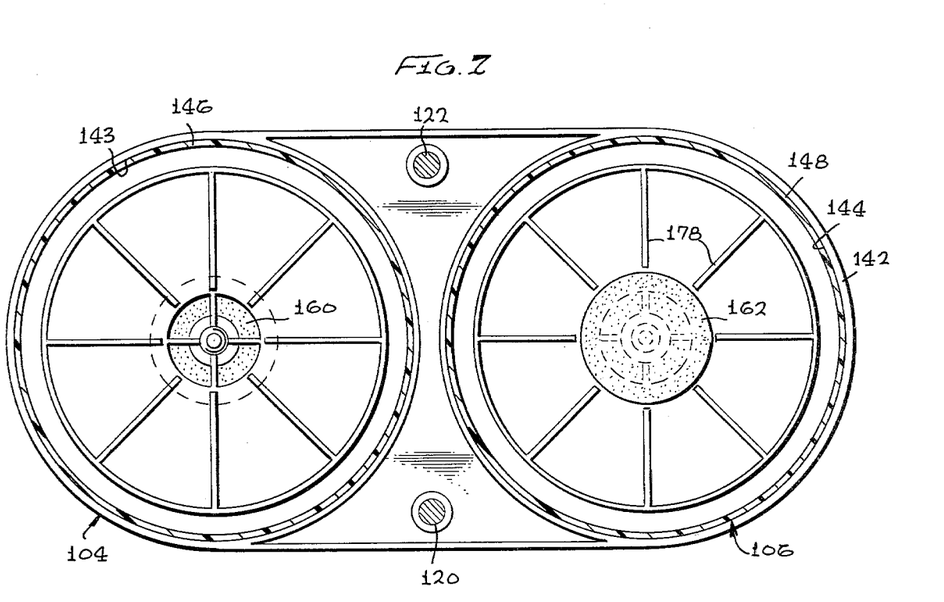
FIG. 7 is a sectional view taken substantially along the plane 7—7 of FIG. 4.

Referring primarily to FIGS. 4 and 7, it can be seen that the cover part 100 comprises a cover plate 140 having a depending apron 142. As is best shown in FIG. 7, the apron 142 is formed so as to define two circular wells 143 and 144 which respectively receive the cylindrical walls 146 and 148 of the canisters 104 and 106. Nipples 150 and 152 extend from the cover plate 140 and open into the wells 143 and 144. More particularly, nipple 150 is aligned with an air outlet opening 156 communicating with well 143. Nipple 152 is aligned with an air inlet opening 158 communicating with well 144. A one way flow valve 160 is mounted in air outlet opening 156 to permit flow therethrough only in the direction from well 143 to nipple 150. A one way flow valve 162 is mounted in air inlet opening 158 to permit flow only in the direction from nipple 152 to well 144.

The canisters 104 and 106 are comprised of substantially cylindrical walls 146 and 148 and perforated air permeable bottom surfaces 166 and 168. Each of the bottom surfaces supports an air permeable foam like disk 170. A quantity of $CO_2$ absorber material 172 is supported on each disk 170. A second foam like disk 174 is placed on the top of the $CO_2$ absorber material in each canister. Radial walls 178 depending from the undersurface of the cover plate 140 bear against the upper disks 174 to press them against the $CO_2$ absorber material.

The cylindrical walls 146 and 148 of the canisters 104 and 106 depend below the canister bottom surfaces 166 and 168 and are adpated to rest on a shoulder 180 formed along the inner edge of wall 182 of the aforementioned center part 108. Wall 182 is configured to define two circular compartments for respectively receiving canisters 104, 106. The canister walls 146, 148 are preferably tapered inwardly adjacent their upper and lower edges respectively receivable in the aforementioned cover part wells and center part compartments. The surfaces of the wells and compartments are preferably similarly tapered so as to mate in an interference fit with the canister wall surfaces to form an air tight seal therewith.

Center part 108 defines a chamber 190 beneath the bottom surfaces 166 and 168 of the canisters 104 and 106. The chamber 190 defines an air entrance opening 192 opening into passage ways 194 and 196 respectively defined by baffles 198 and 200. The passageways 194 and 196 respectively communicate with passageways defined through central elongated tubes 202 and 204.

Two sets of concentric tubes are secured to the undersurface of the center part 108. More particularly, a first set of tubes includes center tube 2 and tubes 206 and 208 concentric therewith. Similarly, a second set of concentric tubes depending from the undersurface of center part 108 includes center tube 104 and concentric tubes 210 and 212.

The two cup-like members 112 and 114 respectively receive the aforementioned two sets of concentric tubes depending from the undersurface of the center part 108. More particularly, cup-like member 112 is comprised of an outer wall 220 and inner concentric walls 222 and 224. The upper edge of the outer wall 220 is provided with outwardly extending radial tabs 240. The tabs 240 are receivable in slots 242 formed in apron 243 of the center part 108.

In assembling the cup-like members 112 and 114 to the center part 108, the cup-like members are first moved toward the center part 108 so that the tabs 240 clear inwardly projecting radial shelves 244. The cup-like members 112 and 114 are then twisted relative to the center part 108 to move the tabs 240 into the slots 242, bayonet fashion, to lock the tabs 242 in the slot supported by the inwardly projecting shelves 244. Thus, the cup-like members 112 and 114 can be easily secured to and removed from the center part 108 without the utilization of any tools. When the cup-like members 112 and 114 are secured to the underside of the center part 108, the concentric walls of the cup-like members mesh with the concentric tubes depending from the under side of the center part 108 to define a flow path comprised of a series of short segments extending from the passageways 194 and 196 to overflow openings 250 defined in the center part 108. For example, a first path is defined within cup-like member 112 down the center of tube 202 and then between tube 202 and wall 224, and then between wall 224 and tube 206, and then between tube 206 and wall 222 and then between wall 222 and tube 208, and then between tube 208 and outer wall 220 to the overflow opening 250. Note that the undersurface of center part 108 is rounded at 260, as is the internal surface 262 of the bottom wall 264 of the cup-like member 112, in order to facilitate smooth air flow along the segmented series flow path defined between the tubes of the center part 108 and walls of the cup-like member 112.

Figures 8, 9, 10:
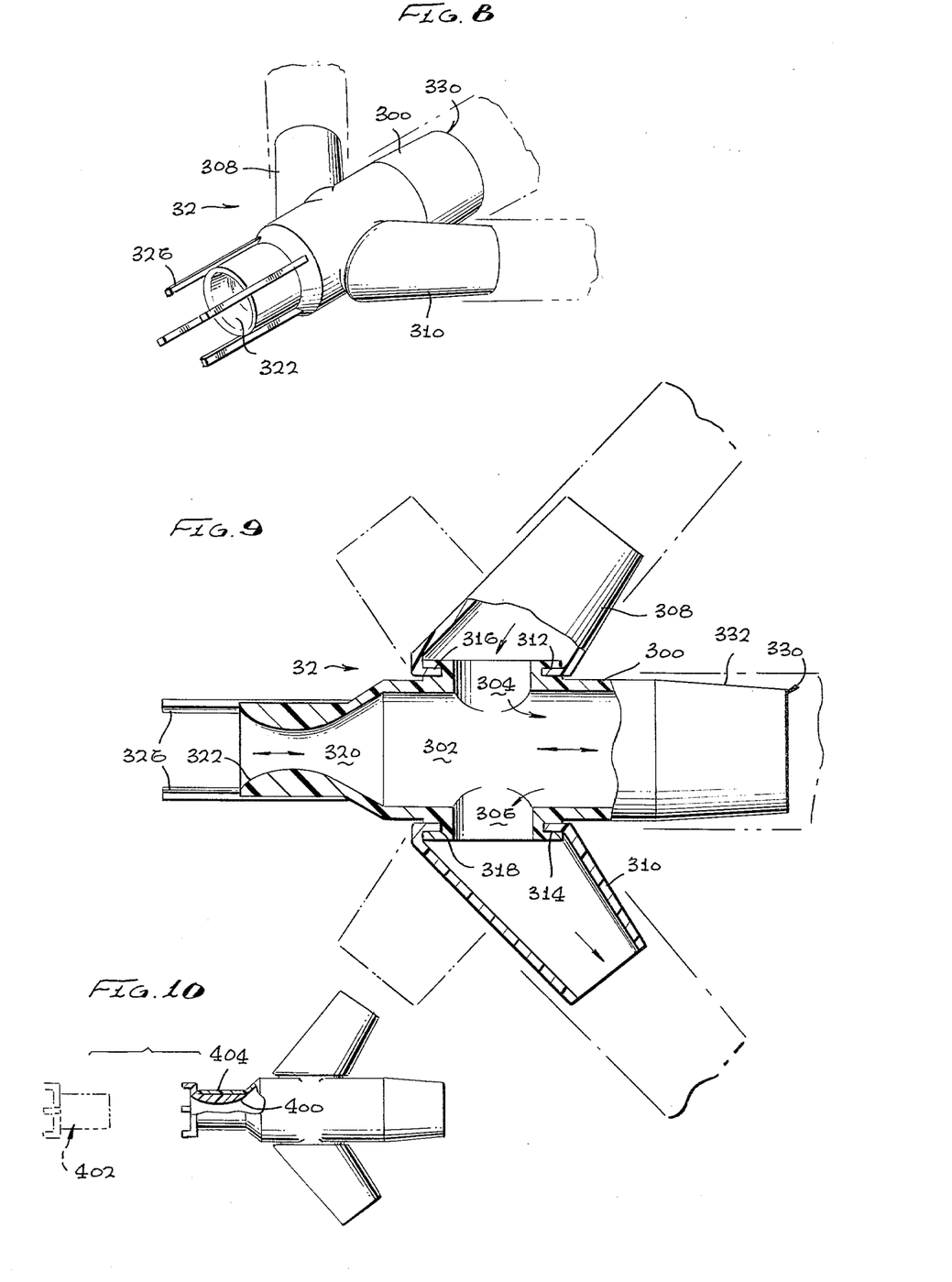
FIG. 8 is a perspective view of a connector in accordance with the invention for coupling the inspiratory and expiratory tubes to a breathing mask.
FIG. 9 is a sectional view taken through the connector of FIG. 8.
FIG. 10 is a plan view, partially broken away, showing an alternative connector.

Attention is now directed to FIGS. 8 and 9 which illustrate the connector 32 (FIG. 1) for coupling the inspiratory and expiratory tubes 18, 16 to the users airway. The connector 32 basically comprises a cylindrical body 300 defining an internal air mixing chamber 302 and four ports which communicate with the chamber 302. More particularly, first and second side ports 304 and 306 are defined respectively communicating with tubular arms 308 and 310. Annular slots 312 and 314 are formed in the connector body around the ports 304 and 306. An inwardly projecting annular flange 316 on arm 308 projects into the slot 312 for rotational movement with respect thereto. Thus, the arm 308 can swivel from the solid line position depicted in FIG. 9 to the phantom line position. Similarly, tubular arm 310 is provided with an inwardly directed flange 318 which is received in slot 314 to enable arm 310 to swivel from the solid line position illustrated in FIG. 9. Tubular arms 308 and 310 are preferably tapered toward their ends remote from the connector body 300 in order to receive the female ends of standard breathing hoses thereon. By mounting the arms 308 and 310 for rotational movement as described, a breathing apparatus in accordance with the invention can be conveniently worn by a user adjacent either his front or back.

In addition to ports 304 and 306, connector 32 provides a third port 320 which comprises an orifice having smoothly formed internal wall surfaces 322 defining a throat region. Inasmuch as the cross sectional dimension of the orifice primarily determines the amount of ambient air exhausted during expiration and inspired during inspiration, a particular orifice dimension is selected dependent upon the altitude which it is desired to simulate.

The connector is also provided with guards 326 which project forwardly of the port 320 to prevent any objects from inadvertently clogging the port.

A fourth port 330 is defined by the connector 32 for communicating the internal chamber 302 to the users airway, either directly via the users mouth or through an appropriate breathing mask 30 or mouthpiece (not shown). The external surface 332 of the connector is preferably tapered about the port 330 for receiving the female end of an opening found on a typical breathing mask.

In use, the connector 32 of FIGS. 8 and 9 is tyically connected between a breathing mask 30 and inspiratory and expiratory tubes 18 and 16, as depicted in FIG. 1. The inspiratory and expiratory tubes are in turn connected to the nipples 150 and 152 as depicted in FIG. 4. On expiration, the users expired air will be transferred through port 330 of the connector 32 into internal chamber 302. A portion of the expired air will then be exhausted to the environment through the selectively dimensioned orifice 320. The remainder of the expired air will flow through port 306, through expiration tube 16, past expiratory valve 162 and through the $CO_2$ absorber material in canister 106. After passing through the air permeable bottom surface 168 of cannister 106, the expired air will flow into the entrance opening 192 and thence into the segmented series flow paths formed in the cup-like members 112 and 114. If the expired air exceeds the capacity of the reservoir defined by the cup-like members, the air will overflow through the overflow openings 250.

On inspiration, the direction of the air movement in the reservoirs will be reversed and the air in the reservoirs will be drawn up through center tubes 202 and 204 through the entrance opening 192 through the chamber 190 and thence through the $CO_2$ absorber material 146, through the inspiratory valve 160, through the inspiratory tube 180, and through port 304, into the chamber 302 in the connector 32. The air drawn into the chamber 302 via the port 304 is mixed with ambient air drawn into the chamber 302 via port 320. The ratio of the ambient air drawn through port 320 to the rebreathed air drawn through port 304 depends upon the relative flow resistances which are in large measure dependent upon the dimension of the port 320. The greater the ratio of ambient air to rebreathed air, the lower will be the altitude simulated by the breathing apparatus. On the other hand, the smaller the ratio of ambient air to rebreathed air, the higher will be the simulated altitude.

It should be noted that the air flow paths formed by the apparatus, as is best depicted in FIGS. 4 and 9, are defined by smoothly radiused surfaces offering a minimum of air flow resistance. Additionally, it should be noted that in the embodiment depicted, the expiration path and inspiration path include like amounts of $CO_2$ absorber material and that the paths are substantially balanced, i.e. exhibit essentially the same resistance to air flow. As a consequence, the user is able to breath through the apparatus without experiencing any significant pressure load. Use of the apparatus, however, will of course produce a physiological stress on the user attributable to the reduction in oxygen available to him as compared with that normally provided by the ambient air. Although it is preferble to include $CO_2$ absorber material in both the inspiration and expiration paths, embodiments of the invention can also be utilized with $CO_2$ absorber material in only one of the paths.

By locating the exhaust port 320 proximate to the user, a selected portion of the users expired air will be exhausted immediately and will not have to be transported by the expiratory tube 16 or stored by the reservoir. As a consequence, the capacity of the expiratory tube 16 and reservoir 24 can be minimized to thereby acheive a structure sufficiently compact to be readily carried by the user while performing light exercise. If the users expired air volume exceeds the capacity of the expiratory tube 16 and reservoir, the excess expired air will overflow through overflow openings 250. On inspiration, the air stored in the reservoir which has not overflowed will be first inspired and will be followed by ambient air drawn into the reservoirs from the overflow openings 250.

The ability of the $CO_2$ absorber material 172 to absorb $CO_2$ diminishes with use. Accordingly, the material 172 must be periodically replaced. This is easily accomplished of course by removing the bolts 120 and 122 which pass through holes 340 in the cover part 100 into threaded bosses 342 in the center part 108. With the bolts 120 and 122 removed, the cover part 100 can be lifted off the cannisters 104 and 106. The canisters can then be removed from the center part 108. The foam like disk 174 can then be removed and the $CO_2$ absorber material can be disposed of and the canisters refilled with fresh material prior to reassembly. In order to conserve $CO_2$ absorber material, it is not generally necessary to dispose of the $CO_2$ absorber material in the inspiratory flow path, i.e. in canister 104. Rather, since the ability of the material to absorb $CO_2$ in the expiratory path canister 106 will diminish more rapidly than the material in the inspiratory path canister 104, $CO_2$ absorber material can be conserved by disposing of the material in canister 106, transferring the canister 104 to the expiratory path, refilling the canister 106 with fresh $CO_2$ absorber material, and then placing the refilled canister in the inspiratory path. Although, the depicted embodiment contemplates that the canisters be refilled with fresh $CO_2$ absorber material, it may be preferable under some circumstances to use disposable nonrefillable $CO_2$ absorber canisters.

It has been pointed out that the dimension of the exhaust port 320, depicted in FIG. 9, primarily establishes the altitude which is simulated by the breathing apparatus. In order to assure maximum safety of the system by a totally inexperienced user, the dimension of the port 320 is fixed at a modest altitude level which provides only a moderate amount of physical stress. Experienced users desiring to simulate higher altitudes can choose connectors 32 having an exhaust port 320 of smaller dimension. On the other hand, an alternative connector embodiment, as depicted in FIG. 10, can be used wherein the exhaust orifice 400 is defined by a removable insert 402 which fits within a substantially cylindrical sleeve 404 of the connector of FIG. 10.

Figure 11:
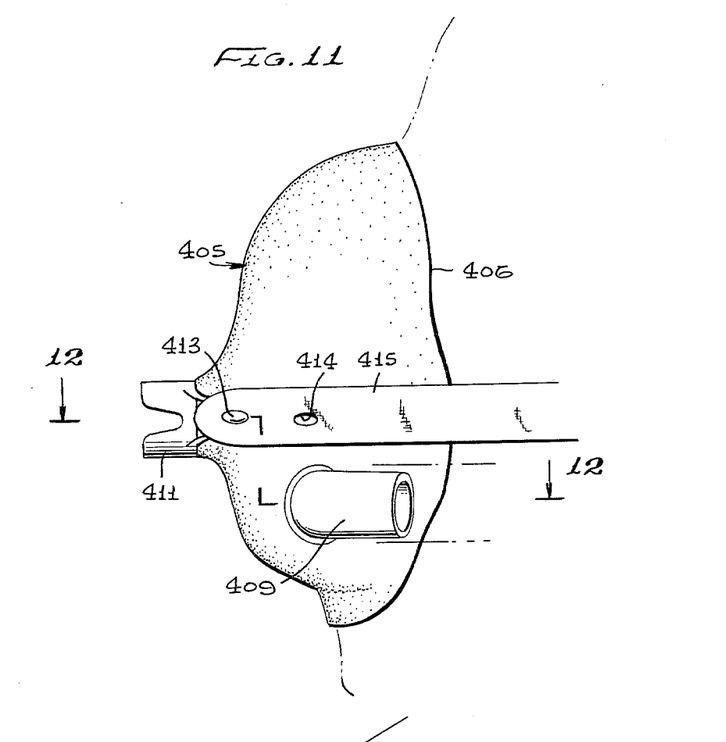
FIG. 11 is a side view of an alternative user breathing means.
Figure 12:
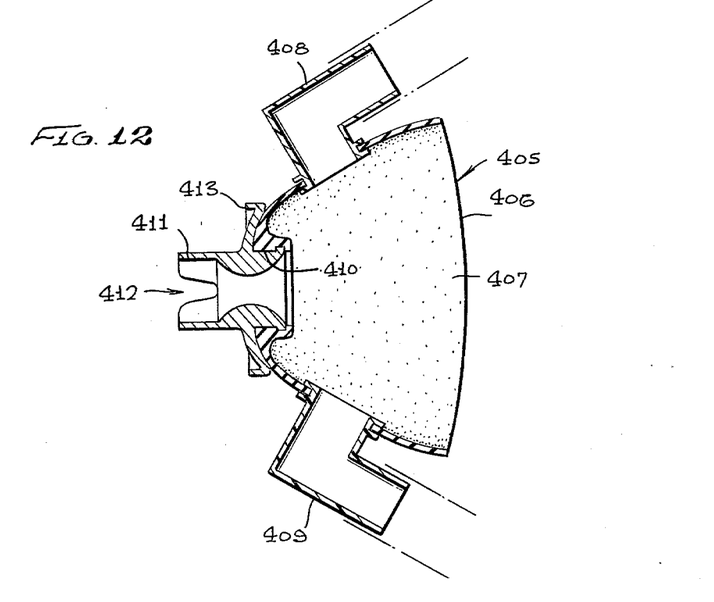
FIG. 12 is a sectional view taken substantially along the plane 12—12 of FIG. 11.

FIGS. 11 and 12 illustrate an alternative user breathing means in which the functions of the aforementioned connector and breathing mask are combined in a single unit. More specifically, the breathing means of FIGS. 11 and 12 includes a semirigid mask 405 adapted to fit over a users nose and mouth. The mask 405 preferably has a compliant edge 406 adapted to fit and conform to the contours of the users face so as to define a substantially sealed internal chamber 407. The chamber 407 communicates through ported arms 408, 409 to inspiratory and expiratory breathing tubes. These arms 408, 409 are preferably mounted for swivel movement relative to the mask 405 to facilitate wearing by the user.

The mask 405 defines a port 410. An insert 411 is retained in the port 410 and defines a selectively dimensioned orifice 412 open to the environment. The insert 411 is preferably provided with hooks 413 which are receivable in eyelets 414 of a strap 415 adapted to extend around the users head to retain the mask 405 on the users face. The mask 405 is used in the same manner as has already been discussed in connection with the embodiment of FIGS. 1-9.

Figure 13:
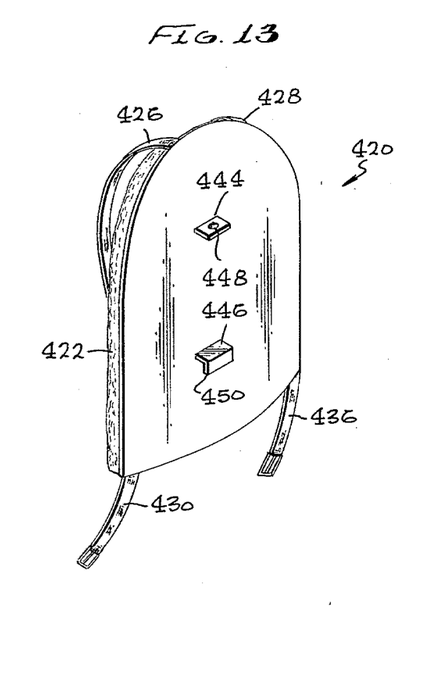
FIG. 13 is a perspective view of a backpad particularly suited for carrying an apparatus in accordance with the invention.
Figure 14:
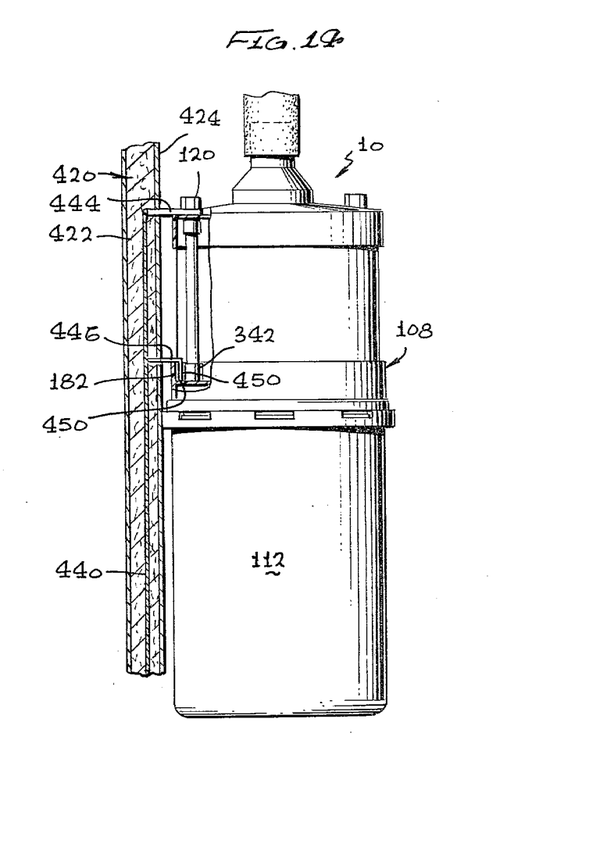
FIG. 14 is a sectional view illustrating the apparatus mounted on the backpad of FIG. 11.

Attention is now directed to FIGS. 13 and 14 which illustrate a back pad assembly 420 for facilitating the carrying of the breathing apparatus on the back of a user. The back pad assembly 420 is comprised of a pad 422 of flexible material, such as a suitable foam material. A fabric cover 424 is sewn around the foam pad 422 to protect it. A pair of shoulder straps 426 and 428, as well as a pair of belt straps 430 and 432 are anchored to the pad and function in the same manner as they do in conventional commercially available backpacks. A suitable frame structure 440 is provided and is preferably buried within the pad layer 422. Secured to the frame structure 440 and extending outwardly from the rear of the back pad assembly 420 is a bracket 444 and a clip 446. A hole 448 is formed in the bracket. The clip 446 has a depending forward lip 450. In use, the breathing apparatus 10 is mounted on the back pad assembly 420 as depicted in FIG. 14. More particularly, the bolt 120 extends through the opening 448 in bracket 444 and thence through the opening 341 in the cover part 100 and thence into the threaded boss 342. The depending lip 450 on clip 446 extends around the upstanding wall 182 of the center part 108 to keep the apparatus close to the rear surface of the back pad assembly 420. The weight of the back pad assembly, as depicted in FIG. 14, is entirely supported by the bolt 120 threaded into the boss 342.

The apparatus disclosed herein can be readily constructed of relatively inexpensive molded plastic parts. It can be assembled and disassembled rapidly by an inexperienced user without any tools. Disassembly and reassembly is periodically required to clean and to replace the $CO_2$ absorber material. The frequency of replacement depends upon various factors but primarily upon the frequency of usage. As is readily known, a need to replace the $CO_2$ absorber material is typically indicated by a change in the color of the material.

Accordingly, it should be appreciated that an improved breathing method and apparatus has been disclosed herein which enables a user to simulate breathing conditions at higher altitudes. Moreover, the apparatus as disclosed herein can be manufactured at relatively low cost and in a compact configuration and can be safely carried and used while performing light exercise.

What is claimed is:

1. Apparatus for supplying an air mixture for inspiration by a user comprised solely of the user's previously expired air and ambient air, which mixture has a lower oxygen concentration than the ambient air, said apparatus comprising:
    inspiratory path means having open first and second ends and including valve means therein for permitting air flow only in the direction from said second to said first end;
    expiratory path means having first and second ends and including valve means therein for permitting air flow only in the direction from said first to said second end;
    air reservoir means;
    means coupling said expiratory path means second end to said reservoir means for supplying air thereto;
    means coupling said inspiratory path means second end to said reservoir means for drawing air therefrom;
    $CO_2$ absorber means incorporated in said expiratory and/or inspiratory path means; and
    user breathing means communicating with the first ends of said inspiratory and expiratory path means and including an orifice providing bi-directional flow communication with the environment located between said inspiratory and expiratory valve means proximate to the first ends of said inspiratory and expiratory path means, said orifice and inspiratory and expiratory path means sized to divide flow therebetween for permitting a user during inspiration to draw air through said orifice from the environment to mix with air drawn through said inspiratory path means from said reservoir means and during expiration to exhaust a portion of the user's expired air through said orifice to the environment and a portion through said expiratory path means into said reservoir means.

2. The apparatus of claim 1 wherein said means coupling said inspiratory path means to said reservoir means includes a first $CO_2$ absorber means; and wherein
    said means coupling said expiratory path means to said reservoir means includes a second $CO_2$ absorber means.

3. The apparatus of claim 1 wherein said air reservoir means includes an entrance opening and an overflow opening and further including baffle means for defining a plurality of flow path segments communicating with one another to form a series flow path extending from said entrance opening to said overflow opening.

4. The apparatus of claim 1 wherein said user breathing means includes a mixing chamber for communicating with a user's airway and including first and second ports for respectively communicating with the first ends of said inspiratory and expiratory path means; and wherein
    said orifice communicates said mixing chamber with the environment.

5. The apparatus of claim 4 wherein said breathing means includes a breathing mask adapted to communicate with a users nose and/or mouth.

6. The apparatus of claim 1 wherein said user breathing means includes a housing defining an internal chamber adapted to communicate with a user's airway and including first and second ports communicating with said chamber;
    first and second tubular arms mounted on said housing for respectively coupling said first and second ports to the first ends of said inspiratory and expiratory path means; and wherein
    said orifice is located in said housing communicating said chamber with the environment.

7. The apparatus of claim 6 wherein said first and second tubular arms are mounted on said housing for adjustable positioning with respect thereto.

8. The apparatus of claim 1 including means for varying the dimensions of said orifice.

9. Apparatus for supplying an air mixture for inspiration by a user comprised solely of the user's previously expired air and ambient air, which mixture has a lower oxygen concentration that the ambient air, said apparatus comprising:
    inspiratory path means having open first and second ends and including valve means therein for permitting air flow only in the direction from said second to said first end;
    expiratory path means having open first and second ends and including valve means therein for permitting air flow only in the direction from said first to said second end;
    air reservoir means;
    first $CO_2$ absorber means coupled between said expiratory path means second end and said reservoir means for passing user expired air therethrough;
    user breathing means communicating with the first ends of said inspiratory and expiratory path means and including an orifice providing bi-directional flow communication with the environment located between said inspiratory and expiratory valve means proximate to the first ends of said inspiratory and expiratory path means, said orifice and inspiratory and expiratory path means sized to divide flow therebetween for permitting a user during inspiration to draw air through said orifice from the environment to mix with air drawn through said inspiratory path means from said reservoir means and during expiration to exhaust a portion of the user's expired air through said orifice to the environment and a portion through said expiratory path means into said reservoir means.

10. The apparatus of claim 9 wherein said first and second $CO_2$ absorber means are dimensioned as to exhibit substantially the same amount of air flow resistance.

11. The apparatus of claim 9 wherein said air reservoir means includes an entrance opening and an overflow opening and further including baffle means for defining a plurality of flow path segments communicating with one another to form a series flow path extending from said entrance opening to said overflow opening.

12. A breathing apparatus comprising:
    first and second canisters each having an air permeable bottom surface supporting a quantity of $CO_2$ absorber material in the canister;
    a cover part overlaying said canisters, said cover part including an air inlet aligned with said first canister and an air outlet aligned with said second canister and including valve means for permitting air flow through said air inlet only into said first canister and air flow through said air outlet only out of said second canister;

a center part for supporting said first and second canisters, said center part defining a chamber having an air entrance opening and communicating with the air permeable bottom surfaces of both said first and second canisters;

means for fastening said cover part and center part to one another so as to sandwich said first and second canisters therebetween;

a bottom member defining an air reservoir;

means for securing said bottom member to said air entrance opening so as to communicate said center part with said bottom member air reservoir;

user breathing means including a housing defining an internal chamber adapted to communicate with a user's airway and a bi-directional flow path communicating with the environment; and inspiratory and expiratory tubes respectively coupling said internal chamber to said cover part air inlet and air outlet.

13. The apparatus of claim 12 wherein said bottom member includes a cup-like portion supporting baffles therein;

said center part including baffles projecting into said bottom member cup-like portion and nesting in the baffles thereof to define a plurality of flow path segments communicating with one another to form a series flow path extending from said air entrance opening to an overflow opening communicating with the environment.

14. The apparatus of claim 12 wherein each of said first and second canisters comprises a cylindrical wall and said air permeable bottom surface;

a removable air permeable disk resting on said $CO_2$ absorber material remote from said air permeable bottom surface;
and
means carried by said cover part bearing against said disk to press it against said $CO_2$ absorber material.

15. The apparatus of claim 12 wherein said means for fastening includes at least one bolt extending through both said cover part and center part.

16. In combination with the breathing apparatus of claim 12, means for mounting said apparatus on a users back comprising:

a back pad having shoulder strap means secured thereto;
and
bracket means anchored to said pad for securing said breathing apparatus thereto.

17. The apparatus of claim 12 wherein said user breathing means housing defines first, second and third ports;

tubular means including said inpiratory and expiratory tubes respectively coupling said first and second ports to said air inlet and air outlet;

said third port being open to communicate said internal chamber with the environment.

18. The apparatus of claim 17 wherein said tubular means includes at least one tubular arm in communication with one of said first or second ports and mounted for adjustable positioning with respect to said housing.

* * * * *